(12) United States Patent
Glickel

(10) Patent No.: US 9,220,549 B2
(45) Date of Patent: Dec. 29, 2015

(54) DISTAL RADIUS VOLAR LOCKING PLATE WITH EXTENSION FOR ULNAR VOLAR FRAGMENT

(76) Inventor: Steven Glickel, New York, NY (US)

( * ) Notice: Subject to any disclaimer, the term of this patent is extended or adjusted under 35 U.S.C. 154(b) by 129 days.

(21) Appl. No.: 13/246,211

(22) Filed: Sep. 27, 2011

(65) Prior Publication Data

US 2013/0079828 A1  Mar. 28, 2013

(51) Int. Cl.
*A61B 17/80* (2006.01)
*A61B 17/88* (2006.01)

(52) U.S. Cl.
CPC ....... *A61B 17/8061* (2013.01); *Y10T 29/49826* (2015.01)

(58) Field of Classification Search
CPC ............... A61B 17/80; A61B 17/8004; A61B 17/8061; A61B 17/8085; A61B 17/809; A61B 17/82
USPC .......................................... 606/280–299, 902
See application file for complete search history.

(56) References Cited

U.S. PATENT DOCUMENTS

| 4,651,724 | A |  | 3/1987 | Brerntey et al. |
| 5,674,222 | A |  | 10/1997 | Berger |
| 6,007,536 | A |  | 12/1999 | Yue |
| 6,283,969 | B1 |  | 9/2001 | Grusin et al. |
| 7,655,029 | B2 | * | 2/2010 | Niederberger et al. ....... 606/280 |
| 7,731,718 | B2 | * | 6/2010 | Schwammberger et al. ... 606/71 |
| 2005/0010226 | A1 |  | 1/2005 | Grady, Jr. et al. |
| 2009/0275991 | A1 | * | 11/2009 | Medoff .......................... 606/297 |
| 2010/0137866 | A1 | * | 6/2010 | Gelfand ........................... 606/70 |
| 2013/0060251 | A1 | * | 3/2013 | Eglseder, Jr. ................... 606/71 |

FOREIGN PATENT DOCUMENTS

| WO | WO03047416 | 6/2003 |
| WO | WO2005034780 | 4/2005 |

OTHER PUBLICATIONS

Jorge Orbay MD "Volar Plate Fixation of Distal Radius Fractures", Hand Clin 21 (2005) p. 347-354.

* cited by examiner

*Primary Examiner* — Kevin T Truong
*Assistant Examiner* — Tracy Kamikawa
(74) *Attorney, Agent, or Firm* — Mark M. Friedman

(57) ABSTRACT

A distal radius fixation plate for volar plating may comprise a distal radius fixation plate body configured to be placed adjacent a fractured volar distal radius and proximal to a watershed line of the volar distal radius and a distal radius fixation plate extension approximately 60 to 80% thinner on average than the distal radius fixation plate and projecting from the distal radius fixation plate body and configured to be placed so that it extends distal to the watershed line, the plate extension configured to curve around an ulnar/volar corner of the distal radius bone so as to engage the volar lip preferably without curving around other parts of the volar lip of the distal radius. The plate extension may have a hook at its upper end. The plate body may have an obliquely angled screw hole to buttress a radial styloid fragment.

15 Claims, 3 Drawing Sheets

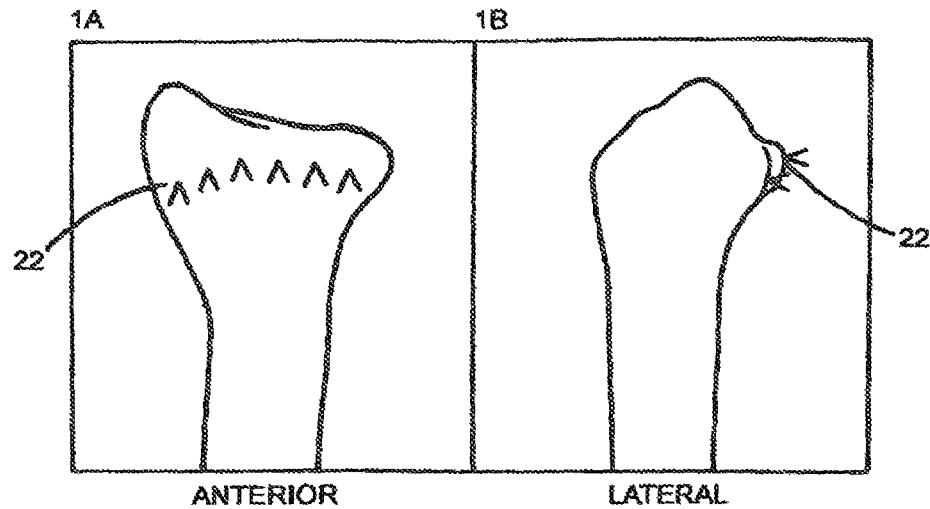
FIG. 1
PRIOR ART
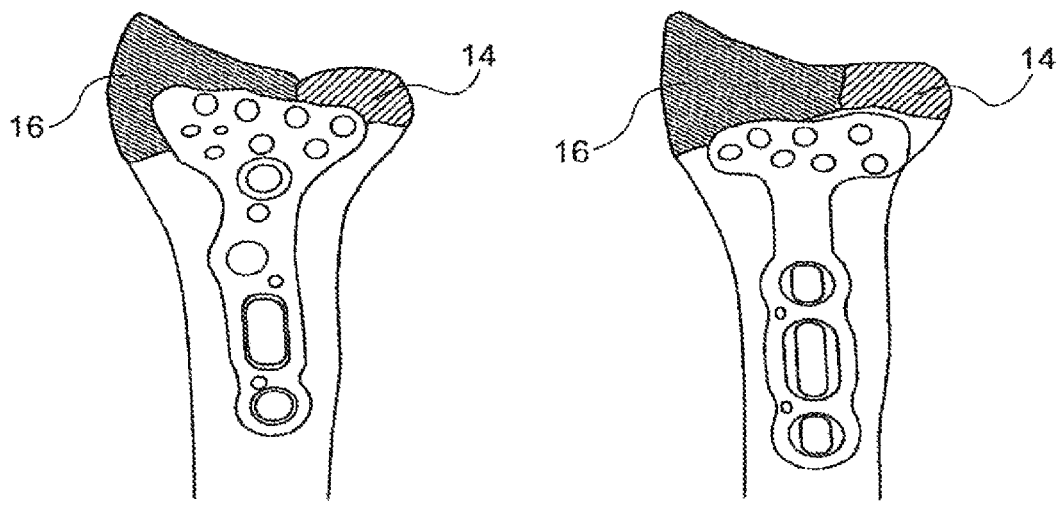
FIG. 2
(PRIOR ART)
FIG. 3
(PRIOR ART)

| METHOD - 100 |
|---|

| POSITIONING A DISTAL RADIUS FIXATION PLATE BODY ALONGSIDE A VOLAR DISTAL RADIUS OF THE FRACTURED DISTAL RADIUS BONE SO THAT THE DISTAL RADIUS FIXATION PLATE IS PROXIMAL TO THE WATERSHED LINE OF THE DISTAL RADIUS BONE, THE DISTAL RADIUS FIXATION PLATE HAVING A PLATE BODY AND A PLATE EXTENSION, THE PLATE EXTENSION AT LEAST 20% THINNER ON AVERAGE THAN THE PLATE BODY |
|---|

110

| ANCHORING THE PLATE EXTENSION TO AN ULNAR VOLAR FRAGMENT BY POSITIONING THE PLATE EXTENSION SO THAT IT PROTRUDES DISTAL TO THE WATERSHED LINE AT THE ULNAR VOLAR CORNER OF THE DISTAL RADIUS BONE |
|---|

DISTAL RADIUS VOLAR LOCKING PLATE WITH EXTENSION FOR ULNAR VOLAR FRAGMENT

FIELD AND BACKGROUND OF THE INVENTION

The present invention relates to apparatuses and methods used in medical treatment of a distal radius fracture, and, more particularly, to such apparatuses and methods in which an extension from a volar fixation plate beyond the watershed line is used.

The forearm has two large bones, the radius and the ulna, which run parallel to one another. The proximal end of the radius is at the lateral side of the elbow and extends all the way to the thumb side of the wrist which is the distal end of the radius (from a reference position in which the palm of the hand faces forward). The radius can also be divided in its other dimensions. For example the palm side of the radius bone is called the "volar" and the other side is called "dorsal". The volar distal radius therefore refers to the palm side of the distal radius. The most prominent region (the part that sticks out like a ridge line) of the volar distal radius is called the "watershed line". A distal radius fracture is a common bone fracture of the distal end of the radius in the forearm, next to the wrist joint. FIG. 1 shows a "watershed line" 15 across a distal radius.

Surgical implantation of a fixation plate to guide healing of the bone has helped revolutionize treatment of distal radius injuries. The plate is fixed adjacent to the bone to be healed and is held in place using screws. There are many different techniques for treating distal radius fractures including dorsal plating, fragment specific fixation, non-spanning external fixation, volar plating, spanning internal fixation plates.

Locked volar plating is a commonly used technique that has significantly improved the value of treatment by offering a patient with a distal radius fracture early return to work, normal lifestyle, etc. The volar fixation plate is implanted in the body and placed adjacent to but external to the volar side of the radius bone. The volar plate has holes and is affixed by screws that run through holes in the plate. There are two types of screws which are used with these plates, non-locking and locking. Non-locking screws are like traditional screws with a normal appearing head. They only fix to the bone and not to the plate. Locking screws have a smaller diameter head which is threaded. The head of a locking screw locks to the plate within one of the holes in the plate. Locking and non-locking screws typically are placed perpendicular or within a range of approximately 15 degrees from perpendicular to the surface of the plate i.e. they can have a somewhat variable angle within which they can lock to the plate.

Notwithstanding its value, a well known complication of volar plating is irritation and/or rupture of the tendons, especially flexor tendons. The idea is to keep the bone fragments of the fracture together securely without causing irritation or rupture of the tendons. The most common way to position the volar plate is to position it at or just proximal to the watershed line of the distal radius, as shown in FIG. 3 (prior art). This has the advantage that it minimizes the risk of flexor tendon irritation that arises if the plate is distal to the watershed line. An alternative place to position the plate is distal to the watershed line of the distal radius, as shown in FIG. 2 (prior art).

There is a well known concern the art to avoid having volar fixation plates project beyond or above the watershed line. For example, as advocated by a prominent orthopedic surgeon, in Volar Plate Fixation of Distal Radius Fractures by Jorge Orbay, M.D., Hand Clinic 21 (2005) 347-354 at page 348, it states that a "properly designed volar plate must provide sufficient distal buttressing to control the volar marginal fragment but must not project beyond or above the watershed line to prevent contact with flexor tendons." Since flexor tendons pass directly over the watershed line, they can be chronically irritated by the metal plate and ultimately rupture if the plate is distal to the watershed line. In fact, the Journal of Bone and Joint Surgery reported that a more distally placed plate is associated with a 4% risk of flexor tendon rupture compared to 0% for a more proximally placed plate design. Flexor tendon rupture is a serious and dreaded complication of distal radius fixation, and is occurring with greater frequency since the advent of volar locking plates (although it can also occur as a complication of dorsal plating if a screw protrudes through the volar cortex of the radius).

However, when the distal radius fracture has small bone fragments, for example in the volar/ulnar corner, many orthopedic surgeons feel that a plate proximal to the watershed line will not capture the fragment so it is necessary to put the volar locking plate distal to the watershed line or add additional forms of fixation to support these small but very important bone fragments at the distal part of the fracture, especially at the volar/ulnar corner. The small bone fragments at the ulnar/volar corner are critical for joint stability. The volar/ulnar corner is hard to buttress or secure with a screw. However, Dr. Orbay, the previously mentioned orthopedic surgeon who advocates positioning the volar plate proximal to the watershed line maintains that the preferred position of the volar plate is proximal to the watershed line even in the case of small volar rim bone fragments since he maintains that these small bone fragments can be adequately supported by use of a K-wire technique. However, if K-wires are used in volar plating the wrist must be immobilized until the fracture is adequately healed, which is usually 6 weeks in contrast to the 2 weeks required if rigid fixation with a plate and/or screws is used. K-wires can also be potential passages for bacteria, can break or bend, can lose fixation and can migrate. In addition, for very small but critical bone fragments, the K-wire technique is not entirely effective because it does not provide rigid fixation like a screw does.

There is a compelling need to have a distal radius fixation plate that avoids flexor tendon irritation but which is secure enough to provide fixation for the small but very important bone fragments of the volar/ulnar corner of the radius that are critical for joint stability and to do so without the disadvantages of the prior art.

SUMMARY OF THE PRESENT INVENTION

One aspect of the present invention is a distal radius fixation plate for volar plating, comprising a distal radius fixation plate body configured to be placed adjacent a fractured volar distal radius and proximal to a watershed line of the volar distal radius; and a distal radius fixation plate extension which is at least 20% thinner on average than the distal radius fixation plate and projecting from the distal radius fixation plate body and configured to be placed so that it extends distal to the watershed line, the plate extension configured to curve around an ulnar/volar corner of the distal radius bone without curving around other parts of the volar lip of the distal radius.

A further aspect of the present invention is a distal radius fixation plate, comprising a distal radius fixation plate body configured to be placed adjacent a fractured volar distal radius and proximal to a watershed line of the volar distal radius, the distal radius fixation plate body having an obliquely angled screw hole alongside a proximal portion of a radial styloid fragment; and a distal radius fixation plate extension thinner than and projecting from the distal radius fixation plate body and configured to be placed so that it extends distal to the watershed line at the ulnar volar corner of the distal radius bone.

A still further aspect of the present invention is a method of volar plate fixation on a fractured distal radius bone, comprising positioning a distal radius fixation plate body alongside a volar distal radius of the fractured distal radius bone so that the distal radius fixation plate is proximal to the watershed line of the distal radius bone, the distal radius fixation plate having a plate body and a plate extension, the plate extension at least 20% thinner on average than the plate body; and anchoring the plate extension to an ulnar volar fragment by positioning the plate extension so that it protrudes distal to the watershed line at the ulnar volar corner of the distal radius bone.

These and other features, aspects and advantages of the present invention will become better understood with reference to the following drawings, descriptions and claims.

BRIEF DESCRIPTION OF THE DRAWINGS

Various embodiments are herein described, by way of example only, with reference to the accompanying drawings, wherein:

FIGS. 1A and 1B are anterior and lateral photographs of a distal radial model designating the watershed line using arrowheads;

FIG. 2 is a photograph of a prior art left volar distal radial plate at the position of best fit on a model distal to the watershed line;

FIG. 3 is a photograph of a prior art left volar distal radial plate, different from FIG. 3, at its position of best fit on a model proximal to the watershed line;

FIG. 6 is a flow chart showing a method in accordance with one embodiment of the present invention.

DETAILED DESCRIPTION OF THE INVENTION

Figure 4:
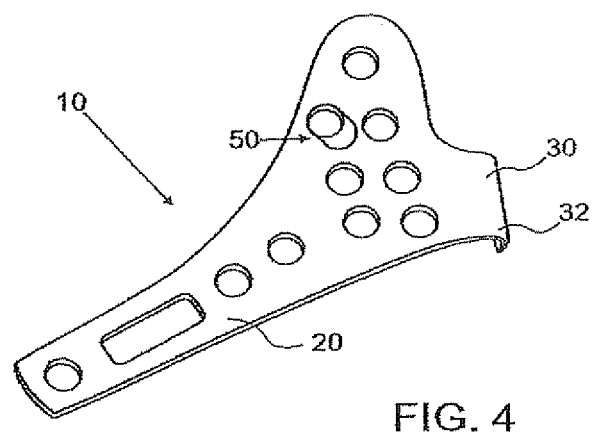
FIG. 4 is an oblique view of a distal radius plate, in accordance with one embodiment of the present invention.

The following detailed description is of the best currently contemplated modes of carrying out the invention. The description is not to be taken in a limiting sense, but is made merely for the purpose of illustrating the general principles of the invention, since the scope of the invention is best defined by the appended claims.

The present invention generally provides a distal radius fixation plate that may include a distal radius fixation plate body that may be configured to be placed proximal to a watershed line of a volar distal radius as well as a distal radius fixation plate extension that may be approximately 60% to 80% as thick on average as the distal radius fixation plate body. The extension plate may project from the distal radius fixation plate body and may be configured to be placed so that it extends distal to the watershed line. The extension plate may also be configured to protrude alongside an ulnar/volar corner of the distal radius bone. The extension plate may have an upper end having a hooked cross-section. The hook may curve around a little more than 90 degrees (approximately 100 to 110 rotational degrees in some preferred embodiments) so as to engage the volar lip of the distal radius. The hook may wrap around the distal edge of the ulnar/volar corner. In preferred embodiments, the extension plate may not protrude past the watershed line into other parts of the volar distal radius besides the ulnar/volar corner. A screw may be used to further buttress the extension plate. In addition, the distal radius fixation plate body may have an obliquely angled hole such as a recessed screw hole alongside a proximal portion of a radial styloid fragment to provide fixation of that fragment without the need for a separate fixation device in addition to the plate.

In contrast to prior art fixation plates for distal radius fractures in which the plate is situated either proximal or distal to the watershed line, the fixation plate of the present invention may be situated proximal to the watershed line while simultaneously having a plate extension that may be situated distal to the watershed line. In contrast to prior art fixation plates in which the fixation plate is situated proximal to the watershed line and is not effective in treating fractures having an ulnar volar corner fragment, the fixation plate of the present invention may include an extension that is designed to buttress the ulnar volar corner fragment. While being secure enough to buttress the ulnar volar corner, the volar fixation plate of the present invention may simultaneously avoid tendon irritation. In further contrast to prior art fixation plates for distal radius fractures in which the plate extends distal to the watershed line but the plate carries a significant increased risk of flexor tendon irritation, the distal radius fixation plate of the present invention may avoid increased risk of flexor tendon irritation even though it may have an extension that may extend distal to the watershed line. For one thing, the extension plate may be made thinner than the body of the fixation plate in order to minimize the volume of material beyond the watershed line. For example, it may be approximately 20-40% thinner on average. In further contrast to the prior art fixation plates, which may not have a hooked cross-section designed to buttress the ulnar volar corner fragment, the fixation plate of the present invention may include an extension plate that may be configured to have a hook at the distal end so as to further anchor fragments in the ulnar volar corner. In still further contrast to prior art fixation plates in which screws may be perpendicular to the body of the plate, in some preferred embodiments the fixation plate of the present invention may include a screw positioned into an obliquely angled screw hole to further buttress a radial styloid fragment. In still further contrast to the prior art volar fixation plates, which may primarily rely on screws or K-wires to secure the ulnar volar corner while leaving the plate body proximal to the watershed, but which may thereby risk migration or loss of fixation of the screw or K-wire, breakage or the creation of a passage for bacteria, the plate extension with a hooked upper end may avoid these complications while still minimizing or avoiding tendon irritation and being secure enough to buttress the ulnar volar corner. In addition, the K-wire fixation of the prior art is not rigid so the wrist would have to be immobilized for approximately 6 weeks whereas the rigid fixation of the plate and hooked plate extension of the present invention may only require 2 weeks of immobilization.

The principles and operation of a distal radius fixation plate with extension for ulnar volar fragment, according to the present invention may be better understood with reference to the drawings and the accompanying description.

The terms "about" and "approximately" as used in this patent application mean plus or minus 10%.

FIGS. 1A and 1B are anterior and lateral photographs of a distal radial model designating the watershed line using arrowheads as they appeared in the Journal of Bone & Joint Surgery Volume 93A Number 4 Feb. 16, 2011 as part of an article entitled "Volar Locking Plate Implant Prominence and Flexor Tendon Rupture".

As seen from FIG. 4, a distal radius fixation plate 10 may comprise a distal radius fixation plate body 20 configured to be placed adjacent a fractured volar distal radius (i.e. a fractured distal radius on the volar side of the radius) and proximal to the watershed line 22 (see FIG. 1) of the volar distal radius 24 (see FIG. 6). As seen from FIG. 1A-B, the watershed line 22 is the most prominent part of the volar distal radius 24—it sticks out like a ridge. Plate 10 may be a volar plate in that it may be configured to be positioned alongside the volar radius. Plate 10 may also include a distal radius fixation plate extension 30 that may be thinner on average than the distal radius fixation plate body 20 and that may project distally from distal radius fixation plate body 20.

As shown in FIGS. 2 and 3, the area distal to the watershed line of the distal radius fracture may include the ulnar volar corner 14 (see FIG. 3 and FIG. 6) and the radial styloid fragment 16 (see FIG. 2).

Extension 30 may be configured so that it may be positioned so as to extend distal to the watershed line 22 (see watershed line in FIGS. 1A-1B) Extension 30 may in particular be configured so that it may be positioned distal to the watershed line 22 at the ulnar volar corner of the distal radius bone. Extension 30 may also be configured so as to be positioned adjacent the ulnar/volar corner so as to curve around the ulnar/volar corner of the distal radius bone. In some preferred embodiments, the extension 30 may curve around the ulnar/volar corner without curving around or protruding alongside other parts of the volar lip of the distal radius. Accordingly, plate extension 30 may thereby extend distal to the watershed line only at the ulnar volar corner, for example not at the radial styloid.

Figure 5:
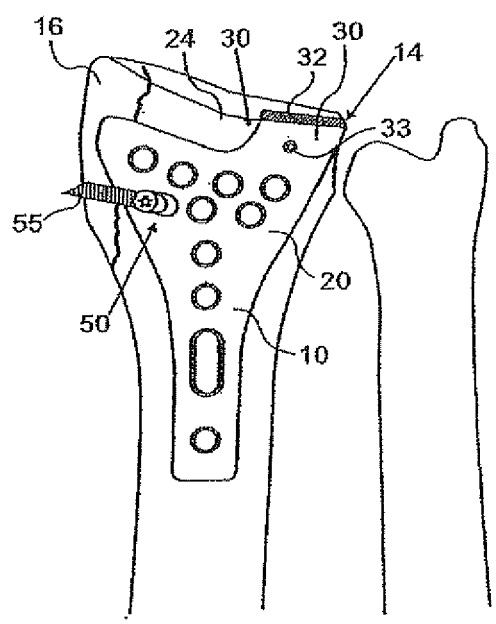
FIG. 5 is a front view of a distal radial plate positioned over a distal radius bone, in accordance with one embodiment of the present invention.

Having the plate extension 30 curve around the ulnar volar corner may be accomplished by configuring the shape of the plate extension 30. As seen from FIG. 5, distal radius fixation plate extension 30 may comprise a hook or may have an upper end 32 that may be hooked and as such may have a hooked cross-section (as seen in FIG. 5). The hooked upper end 32 may be configured to curve around somewhat more than 90 rotational degrees so as to engage a volar lip of the distal radius. In some preferred embodiments, hooked distal end 32 of extension 30 may curve around between approximately 95 and 115 rotational degrees, and in other preferred embodiments, between 100 and 110 rotational degrees, which would allow it to engage the volar lip. The hooked distal end 32 may be configured to curve around or wrap around the ulnar volar corner and engage the volar lip of the distal radius. Plate extension 30 may also be said to have distal end 32 that may be configured to wrap around a distal edge of the ulnar volar corner.

As can be seen clearly from FIGS. 4-6, hooked distal end 32 may curve around to engage the volar lip of the distal radius including along at least a part of the distal end of the radius. As can also be seen from FIGS. 4-6: (i) a continuous width of the hooked distal end 32 may be configured to engage the volar lip across at least a majority of the width of the ulnar/volar corner by following a contour of a curve of the volar lip, (ii) a continuous width of the hooked distal end 32 may be configured to span at least a majority of the entire width, and in other preferred embodiments, at least two-thirds of or an entire width of, the ulnar/volar corner, (iii) a continuous width of the hooked distal end may be at least half as wide as the plate extension at any point along a length of the plate extension and (iv) the plate extension may be integrally joined to the plate body across the entire width of the plate extension at the widest and most proximal part of the plate extension.

So as to minimize material and thereby minimize the risk of tendon irritation and rupture while still being able to securely hold the ulnar volar corner fragments, plate 10 has a plate extension 30 that may be at least 20% less thick on average (or in other preferred embodiments at least 25% or at least 30% or at least 35% or at least 40% less thick on average) than the average thickness of the distal radius fixation plate body 20. In some preferred embodiments, the plate extension 30 may have an average thickness of between 50% and 70%, or in some preferred embodiments, of between 60% to 80% or between 50% to 80% of the average thickness of the distal radius fixation plate body 20. In other preferred embodiments, the plate extension 30 may have an average thickness of no more than 70% an average thickness of the distal radius fixation plate body 20 of the fixation plate, or the plate extension may have an average thickness of no more than 55% or no more than 60% or no more than 65% or or no more than 75% or no more than 80% of the average thickness of the distal radius fixation plate body 20.

In terms of the absolute thickness on average, the plate body 20 may have an average thickness of between 1.5 mm and 2.0 mm or in some preferred embodiments of between 1.5 mm and 1.7 mm. In some preferred embodiments, the plate body 20 may have an average thickness of 1.6 mm or 1.7 mm or 1.8 mm or 1.9 mm. The plate extension 30 may on average be 50 to 80 percent or in some preferred embodiments 60% to 80% or 50% to 70% as thick as the plate body 20 and therefore may have an average thickness of between 0.8 millimeters and 1.4 millimeters or in other preferred embodiments of between 0.8 mm and 1.4 mm or from 0.8 mm to 1.0 mm or in still other preferred embodiments of between 1.05 mm and 1.4 mm. In still some preferred embodiments, especially where plate body 20 has an average thickness of 1.6 mm, the plate extension 30 may have an average thickness of between 1.0 mm to 1.2 mm (or in some embodiments between 0.8 mm and 1.2 mm) or in other preferred embodiments of between 1.0 mm and 1.1 mm (or in some preferred embodiments 0.9 mm and 1.1 mm) or in still other preferred embodiments of between 1.0 mm and 1.12 mm (or in some preferred embodiments 0.8 mm and 1.12 mm). In some preferred embodiments, plate extension 30 may be 1.0 mm in average thickness or may be from 1.0 mm to 1.2 mm or from 1.0 min to 1.3 mm or from 1.0 to 1.4 mm in average thickness.

The average thickness of plate extension 30 may not exceed 80% of the average thickness of plate body 20 and therefore may not exceed 1.2 mm or in some other preferred embodiments may not exceed 1.28 mm or 1.3 mm or 1.4 mm or 1.5 mm or may not exceed 1.6 mm.

In some preferred embodiments, plate extension 30 and/or plate body may have a substantially uniform thickness.

As seen in FIG. 6, which shows plate 10 alongside the distal radius, the distal radius fixation plate body 20 may also have an obliquely angled hole such as a recessed screw hole 50 for an elongated attachment member such as a radial column lag screw 55. The obliquely angled recessed screw hole 50 may be situated alongside a proximal portion of a radial styloid fragment in order to stabilize that fragment and avoid having to add additional hardware besides plate 10. Although plate body 20 of the plate 10 of the present invention may be positioned proximal to the watershed line, it is noted that FIG. 6 is not intended to be precise in showing this and the distal end of the plate body 20 may imprecisely appear in FIG. 6 to extend beyond the watershed line.

As shown in FIG. 4, plate extension 30 may have one or two screw holes 33 for small screws to further buttress the plate extension 30 to the ulnar/volar corner.

Plate 10 may be manufactured as a single piece comprising plate body 20 and plate extension 30. Plate 10 may be made of any suitable material, for example it may be made of titanium. The entire plate 10 may be made of the same material. The methods of manufacture of volar plates are well known in the art and may include making the distal radius fixation plate 20 and plate extension 30 as a product of a single unitary mold, in that they are made together as a single unit of the same material.

The present invention may also be described as a method 100 of volar plate fixation on a fractured distal radius bone. As such, method 100 may include a step 110 of positioning a distal radius fixation plate body alongside a volar distal radius of the fractured distal radius bone so that the distal radius fixation plate is proximal to the watershed line of the distal radius bone, the distal radius fixation plate having a plate body and a plate extension, the plate extension at least 20% thinner on average than the plate body.

In a further step 120, method 100 may also involve anchoring the plate extension to an ulnar volar fragment by positioning the plate extension so that it protrudes distal to the watershed line at the ulnar volar corner of the distal radius bone.

In some preferred embodiments, method 100 may include a step of having a plate extension that is between 20% to 40% thinner on average than the distal radius plate body protrude distal to the watershed line at the ulnar volar corner. In some preferred embodiments, the method 100 may also include a step of using a hooked end of the plate extension to curve around the ulnar volar corner so as to engage a volar lip of the distal radius. The method may further include positioning the plate extension so that it curves around the ulnar volar corner by more than 90 rotational degrees. Method 100 may also have a step in some preferred embodiments of positioning the plate extension so that it curves around the ulnar volar corner by at least 100 rotational degrees, or so that it curves around the ulnar volar corner by at least 90 rotational degrees and by up to 120 rotational degrees, or so that it curves around the ulnar volar corner by between 95 and 115 degrees or by between 100 and 110 rotational degrees or by between 100 and 120 rotational degrees. It should curve more than 90 rotational degrees Method 100 may also include a further step, in some preferred embodiments, of inserting an elongated attachment member such as a screw into an obliquely angled screw hole on the plate body so as to configure the plate body to further buttress a radial styloid fragment of the fractured distal radius bone. Method 100 may also entail a step of further anchoring the plate extension to the ulnar volar fragment by using a small screw in a screw hole 33 in the plate extension.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. A monolithic distal radius fixation plate for volar plating having a longitudinal axis along a length of the plate from a distal end of the plate to a proximal end of the plate, comprising:

a distal radius fixation plate body configured to be placed adjacent a fractured volar distal radius and proximal to a watershed line of the volar distal radius; and a single distal radius fixation plate extension at least 20% thinner on average than the distal radius fixation plate body and projecting from the distal radius fixation plate body and configured to be placed so that the plate extension extends distal to the watershed line, the plate extension comprising a curvilinear distal end and a remainder of the plate extension, the distal end of the plate extension configured to curve around and buttress a volar lip at an ulnar/volar corner of the distal radius with a full length of the plate body adjacent the fractured volar distal radius proximal to the watershed line without the distal end of the plate extension curving around other parts of the volar lip of the distal radius, the distal end of the plate extension being a hooked distal end configured to curve across an external angle more than 90 rotational degrees and up to 120 rotational degrees relative to a distal part of the remainder of the plate extension so as to curve around and engage the volar lip at the ulnar/volar corner, a continuous width of the hooked distal end configured to engage the volar lip across a width of the ulnar/volar corner by following a contour of a curve of the volar lip with minimized risk of irritating or rupturing tendons, wherein the plate is shaped so that the plate extension protrudes distally on an ulnar/volar side of the plate without protruding distally on a radial/volar side of the plate such that the plate is asymmetric along any vertical axis parallel to the longitudinal axis, and wherein the plate body is asymmetric along any vertical axis parallel to the longitudinal axis.

2. The distal radius fixation plate of claim 1, wherein the hooked distal end is configured to engage the volar lip of the distal radius, the hooked distal end configured to curve between 95 and 115 rotational degrees.

3. The distal radius fixation plate of claim 1, wherein the hooked distal end is configured to curve between 100 and 110 rotational degrees.

4. The distal radius fixation plate of claim 1, wherein the plate is shaped so that the plate extension that protrudes distally on the ulnar/volar side of the plate is thinner than any other part of the plate.

5. The distal radius fixation plate of claim 1, wherein the plate extension has an average thickness of between 60% and 80% an average thickness of the distal radius fixation plate body.

6. The distal radius fixation plate of claim 1, wherein the plate extension has an average thickness of no more than 60% an average thickness of the distal radius fixation plate body.

7. The distal radius fixation plate of claim 1, wherein the plate extension has an average thickness of no more than 70% an average thickness of the distal radius fixation plate body.

8. The distal radius fixation plate of claim 1, wherein the plate extension has an average thickness of no more than 65% an average thickness of the distal radius fixation plate body.

9. The distal radius plate of claim 1, wherein the plate extension has an average thickness of between 0.8 millimeters and 1.4 millimeters.

10. The distal radius plate of claim 1, wherein the plate extension has an average thickness of between 1.0 millimeters and 1.2 millimeters.

11. The distal radius plate of claim 1, wherein the plate extension has an average thickness of between 1.0 millimeters and 1.1 millimeters.

12. The distal radius fixation plate of claim 1, wherein the plate extension is integrally joined to the plate body across an entire width of the plate extension at a widest and most proximal part of the plate extension.

13. A monolithic distal radius fixation plate having a longitudinal axis from a distal end of the plate to a proximal end of the plate, comprising:

a distal radius fixation plate body configured to be placed adjacent a fractured volar distal radius and proximal to a watershed line of the volar distal radius, the distal radius fixation plate body having an obliquely angled screw hole configured to be alongside a proximal portion of a radial styloid fragment; and a single distal radius fixation plate extension thinner than and projecting from the distal radius fixation plate body and configured to be placed so that the plate extension extends distal to the watershed line at an ulnar/volar corner of the distal radius, the plate extension comprising a curvilinear distal end and a remainder of the plate extension, the distal end of the plate extension being a hooked distal end configured to curve across an external angle more than 90 rotational degrees and up to 120 rotational degrees relative to a distal part of the remainder of the plate extension so as to curve around and engage a volar lip of the volar distal radius at the ulnar/volar corner while a full length of the plate body is adjacent the fractured volar distal radius proximal to the watershed line without the distal end of the plate extension curving around other parts of the volar lip of the distal radius, a continuous width of the hooked distal end configured to engage the volar lip across a width of the ulnar/volar corner by following a contour of a curve of the volar lip with minimized risk of irritating or rupturing tendons, wherein the plate is shaped so that the plate extension protrudes distally on an ulnar/volar side of the plate without protruding distally on a radial/volar side of the plate such that the plate is asymmetric along any vertical axis parallel to the longitudinal axis, and wherein the plate body is asymmetric along any vertical axis parallel to the longitudinal axis.

14. The distal radius fixation plate of claim 13, wherein the plate extension is between approximately 60% and approximately 80% as thick on average as the distal radius fixation plate body.

15. The distal radius fixation plate of claim 13, the plate extension having a screw hole for further engaging the distal end of the plate extension with the volar lip at the ulnar/volar corner.

* * * * *

UNITED STATES PATENT AND TRADEMARK OFFICE
CERTIFICATE OF CORRECTION

Page 1 of 1

PATENT NO.      : 9,220,549 B2
APPLICATION NO. : 13/246211
DATED           : December 29, 2015
INVENTOR(S)     : Steven Glickel It is certified that error appears in the above-identified patent and that said Letters Patent is hereby corrected as shown below:

In the claims:

Claim 1 column 8 line 20 should be corrected as follows:
Change
 -- con tour --
to
"contour"

Signed and Sealed this
Fifth Day of April, 2016

Michelle K. Lee
*Director of the United States Patent and Trademark Office*